US007833528B2

(12) United States Patent
Griffiths et al.

(10) Patent No.: US 7,833,528 B2
(45) Date of Patent: *Nov. 16, 2010

(54) USE OF MULTISPECIFIC, NON-COVALENT COMPLEXES FOR TARGETED DELIVERY OF THERAPEUTICS

(75) Inventors: Gary L. Griffiths, North Potomac, MD (US); Serengulam V. Govindan, Summit, NJ (US); Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/553,814

(22) Filed: Oct. 27, 2006

(65) Prior Publication Data

US 2007/0048227 A1  Mar. 1, 2007

Related U.S. Application Data

(60) Continuation-in-part of application No. 10/714,391, filed on Nov. 17, 2003, now abandoned, and a continuation-in-part of application No. 11/198,846, filed on Aug. 8, 2005, now Pat. No. 7,560,110, which is a division of application No. 10/150,654, filed on May 17, 2002, now Pat. No. 7,138,103, which is a continuation-in-part of application No. 09/382,186, filed on Aug. 23, 1999, now Pat. No. 7,052,872, which is a continuation-in-part of application No. 09/337,756, filed on Jun. 22, 1999, now Pat. No. 7,074,405.

(60) Provisional application No. 60/426,379, filed on Nov. 15, 2002, provisional application No. 60/104,156, filed on Oct. 14, 1998, provisional application No. 60/090,142, filed on Jun. 22, 1998.

(51) Int. Cl.
*A61K 39/395* (2006.01)
*C12P 21/04* (2006.01)
*C12P 21/08* (2006.01)
*C07K 16/00* (2006.01)

(52) U.S. Cl. .............. 424/136.1; 424/133.1; 424/155.1; 424/156.1; 435/69.6; 530/387.3; 530/388.8; 530/388.85

(58) Field of Classification Search ........................ None
See application file for complete search history.

(56) References Cited

U.S. PATENT DOCUMENTS

| 4,468,457 A | 8/1984 | Goldenberg et al. |
| 4,735,210 A | 4/1988 | Goldenberg |
| 4,737,453 A | 4/1988 | Primus |
| 4,792,521 A | 12/1988 | Shochat |
| 4,818,709 A | 4/1989 | Primus et al. |
| 4,863,713 A | 9/1989 | Goodwin et al. |
| 4,971,792 A | 11/1990 | Steplewski et al. |
| 5,078,998 A | 1/1992 | Bevan et al. |
| 5,101,827 A | 4/1992 | Goldenberg |
| 5,128,119 A | 7/1992 | Griffiths |
| 5,183,756 A | 2/1993 | Schlom |
| 5,225,541 A | 7/1993 | Hackett et al. |
| 5,256,395 A * | 10/1993 | Barbet et al. |
| 5,274,076 A | 12/1993 | Barbet et al. |
| 5,328,679 A | 7/1994 | Hansen et al. |
| 5,469,854 A | 11/1995 | Unger et al. |
| 5,502,037 A | 3/1996 | Kondratyev |
| 5,503,987 A | 4/1996 | Wagner et al. |
| 5,534,254 A | 7/1996 | Huston |
| 5,534,326 A | 7/1996 | Trokhan et al. |
| 5,591,828 A | 1/1997 | Bosslet et al. |
| 5,683,694 A | 11/1997 | Bagshawe et al. |
| 5,693,762 A | 12/1997 | Queen et al. |
| 5,697,902 A | 12/1997 | Goldenberg |
| 5,716,595 A | 2/1998 | Goldenberg |
| 5,746,996 A | 5/1998 | Govindan et al. |
| 5,753,206 A | 5/1998 | McBride et al. |
| 5,772,981 A | 6/1998 | Govindan et al. |
| 5,776,093 A | 7/1998 | Goldenberg |
| 5,776,094 A | 7/1998 | Goldenberg |
| 5,776,095 A | 7/1998 | Goldenberg |
| 5,837,242 A | 11/1998 | Holliger et al. |
| 5,837,243 A | 11/1998 | Deo et al. |

(Continued)

FOREIGN PATENT DOCUMENTS

EP  0263046  4/1988

(Continued)

OTHER PUBLICATIONS

Bardies et al. The Journal of Nuclear Medicine 37(11):1853-1859, 1996.*
Danks et al. Clinical Cancer Research 5:917-924, Apr. 1999.*
Haisma et al. Blood, 92(1):184-190, Jul. 1, 1998.*
Alt et al., "Novel tetravalent and bispecific IgG-like antibody molecules combining single-chain diabodies with the immunoglobulin gamma1 Fc or CH3 region", FEBS Lett. Jul. 2, 1999; 454(1-2):90-4.
Arano et al., "Reassessment of Diethylenetriaminepentaacetic Acid (DTPA) as a Chelating Agent for Indium-111 Labeling of Polypeptides Using a Newly Synthesized Monoreactive DTPA Derivative", J. Med. Chem. 1996, 39, 3451-3460.
Bamias and Epenetos, "Two-Step Strategies for the Diagnosis and Treatment of Cancer with Bioconjugates", Antibody, Immunoconj. Radiopharm., 5(4):385-395, 1992.

(Continued)

*Primary Examiner*—David J. Blanchard
(74) *Attorney, Agent, or Firm*—Richard A. Nakashima

(57) ABSTRACT

Embodiments of the invention relate to a method for treating target cells, tissues or pathogens in a subject, comprising administering a non-covalently bound complex which comprises a multispecific targeting protein and a hapten-enzyme covalent conjugate, followed by administration of a prodrug that is converted to an active drug by the enzyme. Other embodiments of the invention further relate to kits comprising the non-covalently bound complex or the components to prepare the complex.

23 Claims, No Drawings

U.S. PATENT DOCUMENTS

| | | | |
|---|---|---|---|
| 5,846,741 | A * | 12/1998 | Griffiths et al. |
| 5,851,527 | A | 12/1998 | Hansen |
| 5,959,083 | A | 9/1999 | Bosslet et al. |
| 6,010,680 | A | 1/2000 | Govindan et al. |
| 6,077,499 | A | 6/2000 | Griffiths et al. |
| 6,096,289 | A | 8/2000 | Goldenberg |
| 6,121,424 | A | 9/2000 | Whitlow et al. |
| 6,126,916 | A | 10/2000 | McBride et al. |
| 6,187,284 | B1 | 2/2001 | Griffiths |
| 6,217,869 | B1 * | 4/2001 | Meyer et al. |
| 6,540,980 | B1 | 4/2003 | Blumenthal et al. |
| 6,962,702 | B2 | 11/2005 | Hansen et al. |
| 7,074,405 | B1 | 7/2006 | Hansen et al. |
| 7,138,103 | B2 | 11/2006 | Goldenberg et al. |
| 2003/0068322 | A1 * | 4/2003 | Hansen |

FOREIGN PATENT DOCUMENTS

| | | |
|---|---|---|
| EP | 0419387 | 3/1991 |
| EP | 0511011 | 10/1992 |
| EP | 0517024 | 12/1992 |
| EP | 0623675 | 11/1994 |
| IE | 921782 | 12/1992 |
| WO | 9604313 | 2/1996 |
| WO | 9741898 | 11/1997 |
| WO | 9808875 | 3/1998 |
| WO | 9966951 | 12/1999 |
| WO | 0016808 | 3/2000 |
| WO | 0034317 | 6/2000 |
| WO | 0043541 | 7/2000 |

OTHER PUBLICATIONS

Barbet et al., "Radioimmunotherapy of LS174T Colon Carcinoma in Nude Mice Using an Iodine-131-Labeled Bivalent Hapten Combined with an Anti-CEA x Anti-Indium-DTPA Bispecific Antibody", Tumor Biology, 18 (Suppl. 2), p. 31 (1997).

Barbet et al., "Radioimmundetection of medullary thyroid carcinoma using Indium-111 bivalent hapten and Anti-CEA x Anti-DTPA-Indium bispecific antibody", J. Nucl. Med. Jul. 1998; 39(7):1172-8.

Boden et al., "Preliminary Study of the Metal Binding Site of an Anti-DTPA-Indium Antibody by Equilibrium Binding Immunoassays and Immobilized Metal Ion Affinity Chromatography", Bioconjugate Chem. 1995, 6, 373-379.

Bos et al., "In Vitro Evaluation of DNA-DNA Hybridization as a Two-Step Approach in Radioimmunotherapy of Cancer", Cancer Res. 54, 3479-3486, Jul. 1, 1994.

Bosslet et al., "Generation of Bispecific Monoclonal Antibodies for Two Phase Radioimmunotherapy", Br. J. Cancer May 1991; 63(5):681-6.

Chatziioannou et al., "Micropet I: Performance Evaluation of a Very High Resolution PET Scanner for Imaging Small Animals", J. Nucl. Med. 38(5), May 1997 Suppl., No. 19, p. 7P-8P.

Cruse and Lewis, Illustrated Dictionary of Immunology, CRC Press, 1995, p. 117.

De Boisferon et al., "Enhanced Targeting Specificity to Tumor Cells by Simultaneous Recognition of Two Antigens", Bioconj. Chem. 2000, 11, 452-460.

De Jonge et al., Production and Characterization of Bispecific Single-Chain Antibody Fragments, Mol. Immunol. 32 (17/18):1405-1412 (1995).

Dubel et al., "Reconstitution of human pancreatic RNase from two separate fragments fused to different single chain antibody fragments: on the way to binary immunotoxins", Tumor Targeting (1999) 4, 37-46.

Gautherot et al., "Radioimmunotherapy of LS174T Colon Carcinoma in Nude Mice Using an Iodine-131-Labeled Bivalent Hapten Combined with an Anti-CEA x Anti-Indium-DTPA Bispecific Antibody", J. Nucl. Med. 38(5), May 1997 Suppl., No. 18, p. 7P.

Gautherot et al., "Delivery of therapeutic doses of radioiodine using bispecific antibody-targeted bivalent haptens", J. Nucl. Med. Nov. 1998; 39(11):1937-43.

Gautherot et al., "Therapy for colon carcinoma xenografts with bispecific antibody-targeted, iodine-131-labeled bivalent hapten", Cancer Dec. 15, 1997; 80(12 Suppl.):2618-23.

Gold et al., "Murine Monoclonal Antibodies to Colon-specific Antigen p1", Cancer Res. 50, 6405-6409, Oct. 1, 1990.

Goodwin et al., "Pre-targeted immunoscintigraphy of murine tumors with Indium-111-labeled bifunctional haptens", J. Nucl. Med. Feb. 1988; 29(2):226-34.

Greenwood et al., "The Preparation of 131I-Labelled Human Growth Hormone of High Specific Radioactivity", Biochem. J. (1963) 89, 114-123.

Hayden et al., "Single-chain mono- and bispecific antibody derivatives with novel biological properties and antitumour activity from a COS cell transient expression system", Therapeutic Immunology 1994, 1, 3-15.

Hawkins et al., "Delivery of radionuclides to pretargeted monoclonal antibodies using dihydrofolate reductase and methotrexate in an affinity system", Cancer Res. May 15, 1993; 53(10 Suppl.):2368-73.

Hosono et al., "Biodistribution and dosimetric study in medullary thyroid cancer xenograft using bispecific antibody and Iodine-125-labeled bivalent hapten", J. Nucl. Med. Sep. 1998; 39(9):1608-13.

Kaneko et al., "New Hydrazone Derivatives of Adriamycin and Their Immunoconjugates-a Correlation between Acid Stability and Cytotoxicity", Bioconj. Chem. 2(3):133-141 (1991).

Karacay et al., "Studies on a humanized anti-CEA x murine anti-(In-DTPA) bispecific antibody construct for radioimmunotherapy of CEA-positive tumors", Proc. Natl. Acad. Sci. USA, vol. 40, p. 644, Mar. 1999.

Karacay et al., "Pretargeting studies with a humanized anti-CEA x Murine anti(In-DTPA) bispecific antibody construct and Tc-99m/Re-188 labeled peptide", J. Nucl. Med. vol. 40, No. 5 Suppl., p. 225, May 1999.

Karacay et al., "Pretargeting Studies with a Murine Anti-Colon-Specific Antigen-P (CSAp) x Chimeric Anti-[Indium-DTPA] Bispecific Antibody and Technetium-99m-Labeled Peptide", Cancer Biother. Radiopharm. 15(4):412 (2000).

Karacay et al., "Experimental Pretargeting Studies of Cancer with a Humanized anti-CEA x Murine anti-[IN-DTPA] Bispecific Antibody Constructs and a 99mTc-/188Re-Labeled Peptide", Bioconj. Chem. 2000, 11, 842-854.

Kipriyanov et al., "Bispecific tandem diabody for tumor therapy with improved antigen binding and pharmacokinetics", J. Mol. Biol. Oct. 15, 1999; 293(1):41-56.

Kontermann et al., "Intracellular and cell surface displayed single-chain diabodies", J. Immunol. Methods 226 (1999) 179-188.

Kraeber-Bodere et al., "Phase I/II total of two-step radioimmunotherapy in medullary thyroid cancer (MTC) using bispecific anti-CEA/anti-DTPA-in antibody and iodine-131-labeled bivalent hapten", J. Nucl. Med., May 1998, p. 246, vol. 39, No. 5 Suppl.

Kraeber-Bodere et al., "Bispecific antibody and bivalent hapten radioimmunotherapy in CEA-producing medullary thyroid cancer xenograft", J. Nucl. Med. Jan. 1999; 40(1):198-204.

Kranenborg et al., "Two-step radio-immunotargeting of renal-cell carcinoma xenografts in nude mice with antirenal-cell-carcinoma X anti-DTPA bispecific monoclonal antibodies", Int. J. Cancer Jan. 5, 1998; 75(1):74-80.

Kranenborg et al., "Development and characterization of anti-renal cell carcinoma x antichelate bispecific monoclonal antibodies for two-phase targeting of renal cell carcinoma", Cancer Res. Dec. 1, 1995; 55(23 Suppl.):5864s-5867s.

Losman et al., "Generation and Monitoring of Cell Lines Producing Humanized Antibodies", Clin. Cancer Res. 5:3101s-3105s, Oct. 1999 (Suppl.).

Manetti et al., "Intracellular Uptake and Catabolism of Anti-IgM Antibodies and Bi-specific Antibody-Targeted Hapten by B-lymphoma Cells", Int. J. Cancer Oct. 9, 1995; 63(2):250-6.

McGuinness et al., "Phage Diabody Repertoires for Selection of Large Numbers of Bispecific Antibody Fragments", Nat. Biotechnol. Sep. 1996; 14(9):1149-54.

Olafsen et al., "IgM Secretory Tailpiece Drives Multimerisation of Bivalent scFv Fragments in Eukaryotic Cells", Immunotechnology Oct. 1998; 4(2):141-53.

Pack et al., "Tetravalent Miniantibodies with High Avidity Assembling in *Escherichia coli*", J. Mol. Biol. (1995) 246, 28-34.

Paganelli et al., "Monoclonal antibody pretargeting techniques for tumour localization: the avidin-biotin system", Nuclear Medicine Communications, 12, 221-234 (1991).

Paul, William E., Fundamental Immunology, 3rd Ed., Raven Press, New York, 1993, pp. 292-295.

Penefsky, H., "A Centrifuged-Column Procedure for the Measurement of Ligand Binding by Beef Heart F1", Methods in Enzymology, vol. LVI, Chapt 47, p. 527-530, 1979.

Pluckthun and Pack, "New protein engineering approaches to multivalent and bispecific antibody fragments", Immunotechnology 3 (1997) 83-105.

Schuhmacher et al., "Multistep tumor targeting in nude mice using bispecific antibodies and a gallium chelate suitable for immunoscintigraphy with positron emission tomography", Cancer Res. Jan. 1, 1995; 55(1):115-23.

Sharkey et al., "A Universal Pretargeting System for Cancer Detection and Therapy Using Bispecific Antibody", Cancer Res. 63, 354-363, Jan. 15, 2003.

Sharkey et al., "Development of a streptavidin-anti-carcinoembryonic antigen antibody, radiolabeled biotin pretargeting method for radioimmunotherapy of colorectal cancer. Studies in a human colon cancer xenograft model", Bioconjug. Chem. Jul.-Aug. 1997; 8(4):595-604.

Stickney et al., "Bifunctional antibody: a binary radiopharmaceutical delivery system for imaging colorectal carcinoma", Cancer Res. Dec. 15, 1991; 51(24):6650-5.

Van Spriel et al., "Immunotherapeutic perspective for bispecific antibodies", Immunol. Today Aug. 2000;21(8):391-7.

Wang et al., "Specific Activation of Glucuronide Prodrugs by Antibody-targeted Enzyme Conjugates for Cancer Therapy", Cancer Res. 52, 4484-4491, Aug. 15, 1992.

Yang et al., "A genetically engineered single-chain FV/TNF molecule possesses the anti-tumor immunoreactivity of FV as well as the cytotoxic activity of tumor necrosis factor", Mol. Immunol. 32(12):873-881 (1995).

* cited by examiner

SEQUENCE LISTING

<160> NUMBER OF SEQ ID NOS: 2

<210> SEQ ID NO 1
<211> LENGTH: 1000
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(500)
<223> OTHER INFORMATION: This region may encompass 10 to 500 residues
<220> FEATURE:
<221> NAME/KEY: MOD_RES
<222> LOCATION: (501)..(1000)
<223> OTHER INFORMATION: This region may encompass 10 to 500 residues

<400> SEQUENCE: 1
```

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
            85                  90                  95

Lys Lys Lys Lys Lys Lys Lys Lys Lys Lys Lys Lys Lys Lys Lys Lys
        100                 105                 110

Lys Lys Lys Lys Lys Lys Lys Lys Lys Lys Lys Lys Lys Lys Lys Lys
    115                 120                 125

Lys Lys Lys Lys Lys Lys Lys Lys Lys Lys Lys Lys Lys Lys Lys Lys
130                 135                 140

Lys Lys Lys Lys Lys Lys Lys Lys Lys Lys Lys Lys Lys Lys Lys Lys
145                 150                 155                 160

Lys Lys Lys Lys Lys Lys Lys Lys Lys Lys Lys Lys Lys Lys Lys Lys
            165                 170                 175

Lys Lys Lys Lys Lys Lys Lys Lys Lys Lys Lys Lys Lys Lys Lys Lys
        180                 185                 190

Lys Lys Lys Lys Lys Lys Lys Lys Lys Lys Lys Lys Lys Lys Lys Lys
    195                 200                 205

Lys Lys Lys Lys Lys Lys Lys Lys Lys Lys Lys Lys Lys Lys Lys Lys
210                 215                 220

Lys Lys Lys Lys Lys Lys Lys Lys Lys Lys Lys Lys Lys Lys Lys Lys
225                 230                 235                 240

Lys Lys Lys Lys Lys Lys Lys Lys Lys Lys Lys Lys Lys Lys Lys Lys
            245                 250                 255

Lys Lys Lys Lys Lys Lys Lys Lys Lys Lys Lys Lys Lys Lys Lys Lys
        260                 265                 270

Lys Lys Lys Lys Lys Lys Lys Lys Lys Lys Lys Lys Lys Lys Lys Lys
    275                 280                 285

Lys Lys Lys Lys Lys Lys Lys Lys Lys Lys Lys Lys Lys Lys Lys Lys
290                 295                 300

Lys Lys Lys Lys Lys Lys Lys Lys Lys Lys Lys Lys Lys Lys Lys Lys
305                 310                 315                 320

Lys Lys Lys Lys Lys Lys Lys Lys Lys Lys Lys Lys Lys Lys Lys Lys
            325                 330                 335

Lys Lys Lys Lys Lys Lys Lys Lys Lys Lys Lys Lys Lys Lys Lys Lys

-continued

```
                    340             345             350
Lys Lys Lys Lys Lys Lys Lys Lys Lys Lys Lys Lys Lys Lys Lys
        355             360             365

Lys Lys Lys Lys Lys Lys Lys Lys Lys Lys Lys Lys Lys Lys Lys
    370             375             380

Lys Lys Lys Lys Lys Lys Lys Lys Lys Lys Lys Lys Lys Lys Lys
385             390             395             400

Lys Lys Lys Lys Lys Lys Lys Lys Lys Lys Lys Lys Lys Lys Lys
            405             410             415

Lys Lys Lys Lys Lys Lys Lys Lys Lys Lys Lys Lys Lys Lys Lys
        420             425             430

Lys Lys Lys Lys Lys Lys Lys Lys Lys Lys Lys Lys Lys Lys Lys
    435             440             445

Lys Lys Lys Lys Lys Lys Lys Lys Lys Lys Lys Lys Lys Lys Lys
450             455             460

Lys Lys Lys Lys Lys Lys Lys Lys Lys Lys Lys Lys Lys Lys Lys
465             470             475             480

Lys Lys Lys Lys Lys Lys Lys Lys Lys Lys Lys Lys Lys Lys Lys
            485             490             495

Lys Lys Lys Lys Glu Glu Glu Glu Glu Glu Glu Glu Glu Glu Glu
        500             505             510

Glu Glu Glu Glu Glu Glu Glu Glu Glu Glu Glu Glu Glu Glu Glu
    515             520             525

Glu Glu Glu Glu Glu Glu Glu Glu Glu Glu Glu Glu Glu Glu Glu
530             535             540

Glu Glu Glu Glu Glu Glu Glu Glu Glu Glu Glu Glu Glu Glu Glu
545             550             555             560

Glu Glu Glu Glu Glu Glu Glu Glu Glu Glu Glu Glu Glu Glu Glu
            565             570             575

Glu Glu Glu Glu Glu Glu Glu Glu Glu Glu Glu Glu Glu Glu Glu
        580             585             590

Glu Glu Glu Glu Glu Glu Glu Glu Glu Glu Glu Glu Glu Glu Glu
    595             600             605

Glu Glu Glu Glu Glu Glu Glu Glu Glu Glu Glu Glu Glu Glu Glu
610             615             620

Glu Glu Glu Glu Glu Glu Glu Glu Glu Glu Glu Glu Glu Glu Glu
625             630             635             640

Glu Glu Glu Glu Glu Glu Glu Glu Glu Glu Glu Glu Glu Glu Glu
            645             650             655

Glu Glu Glu Glu Glu Glu Glu Glu Glu Glu Glu Glu Glu Glu Glu
        660             665             670

Glu Glu Glu Glu Glu Glu Glu Glu Glu Glu Glu Glu Glu Glu Glu
    675             680             685

Glu Glu Glu Glu Glu Glu Glu Glu Glu Glu Glu Glu Glu Glu Glu
        690             695             700

Glu Glu Glu Glu Glu Glu Glu Glu Glu Glu Glu Glu Glu Glu Glu
705             710             715             720

Glu Glu Glu Glu Glu Glu Glu Glu Glu Glu Glu Glu Glu Glu Glu
            725             730             735

Glu Glu Glu Glu Glu Glu Glu Glu Glu Glu Glu Glu Glu Glu Glu
        740             745             750

Glu Glu Glu Glu Glu Glu Glu Glu Glu Glu Glu Glu Glu Glu Glu
    755             760             765
```

```
Glu Glu Glu Glu Glu Glu Glu Glu Glu Glu Glu Glu Glu Glu Glu
    770             775             780
Glu Glu Glu Glu Glu Glu Glu Glu Glu Glu Glu Glu Glu Glu Glu
785             790             795             800
Glu Glu Glu Glu Glu Glu Glu Glu Glu Glu Glu Glu Glu Glu Glu
        805             810             815
Glu Glu Glu Glu Glu Glu Glu Glu Glu Glu Glu Glu Glu Glu Glu
            820             825             830
Glu Glu Glu Glu Glu Glu Glu Glu Glu Glu Glu Glu Glu Glu Glu
    835             840             845
Glu Glu Glu Glu Glu Glu Glu Glu Glu Glu Glu Glu Glu Glu Glu
850             855             860
Glu Glu Glu Glu Glu Glu Glu Glu Glu Glu Glu Glu Glu Glu Glu
865             870             875             880
Glu Glu Glu Glu Glu Glu Glu Glu Glu Glu Glu Glu Glu Glu Glu
        885             890             895
Glu Glu Glu Glu Glu Glu Glu Glu Glu Glu Glu Glu Glu Glu Glu
            900             905             910
Glu Glu Glu Glu Glu Glu Glu Glu Glu Glu Glu Glu Glu Glu Glu
        915             920             925
Glu Glu Glu Glu Glu Glu Glu Glu Glu Glu Glu Glu Glu Glu Glu
    930             935             940
Glu Glu Glu Glu Glu Glu Glu Glu Glu Glu Glu Glu Glu Glu Glu
945             950             955             960
Glu Glu Glu Glu Glu Glu Glu Glu Glu Glu Glu Glu Glu Glu Glu
            965             970             975
Glu Glu Glu Glu Glu Glu Glu Glu Glu Glu Glu Glu Glu Glu Glu
        980             985             990
Glu Glu Glu Glu Glu Glu Glu Glu
        995             1000

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Lys Tyr Lys
1
```

USE OF MULTISPECIFIC, NON-COVALENT COMPLEXES FOR TARGETED DELIVERY OF THERAPEUTICS

CROSS-REFERENCE TO RELATED APPLICATIONS

This application is a continuation-in-part of application Ser. No. 10/714,391 (now abandoned), filed Nov. 17, 2003, which claims priority from provisional application Ser. No. 60/426,379, filed Nov. 15, 2002; and is also a continuation-in-part of application Ser. No. 11/198,846, filed Aug. 8, 2005, now U.S. Pat. No. 7,560,110 which is a divisional of application Ser. No. 10/150,654, filed May 17, 2002, now U.S. Pat. No. 7,138,103, which is a continuation-in-part of application Ser. No. 09/382,186, filed Aug. 23, 1999, now U.S. Pat. No. 7,052,872, which is a continuation-in-part of application Ser. No. 09/337,756, filed Jun. 22, 1999, now U.S. Pat. No. 7,074,405, which claims priority from provisional application Ser. No. 60/104,156, filed Oct. 14, 1998 and provisional application Ser. No. 60/090,142, filed Jun. 22, 1998.

SEQUENCE LISTING

The instant application contains a Sequence Listing which has been submitted via EFS-Web and is hereby incorporated by reference in its entirety. Said ASCII copy, created on Jan. 20, 2010, is named 78258341.txt, and is 9,660 bytes in size.

FIELD OF THE INVENTION

The invention relates to a method, a composition and a kit for delivering therapeutic agents to subjects.

BACKGROUND OF THE INVENTION

The selective delivery of therapeutic agents to diseased tissue, in vivo, remains a major challenge in the interests of improved therapeutic outcomes. It must be appreciated that although much of the following discussion of the invention is specified toward anti-cancer treatments, any disease state amenable to treatment with drugs or prodrugs could be addressed in the same way. In the case of cancers, standard chemotherapies have depended, in general, upon the enhanced uptake of toxic drugs by fast-growing diseased cells, in relation to most normal cells. However, this has been found to be only of limited value, and normal cell toxicities are often reached before a decisive therapeutic effect against the cancer can be obtained. Typically, those normal cells that divide the fastest are most prone to the adverse effects of chemotherapy agents.

Several different approaches are being taken that seek to improve the therapeutic outcomes resulting from anti-cancer drug therapies. One is the use of mixtures or 'cocktails' of drugs, with component drugs often chosen for their effects on different aspects of cell metabolism. A second is the encapsulation of drugs into carriers such as liposomes or the attachment of drugs to long-circulating polymers. This approach extends drug half-life in serum, and generally allows for a greater proportion of the administered drug to be deposited at the target site. A third approach can be viewed as an advance on the second approach, in that drugs are attached to specific targeting agents such as monoclonal antibodies or peptides. These agents are able to specifically accrete at a target due to their binding to an antigen or receptor, respectively, which has been upregulated or specifically produced by the target cells.

A disadvantage with the aforementioned approaches is the tendency of drugs to lose potency upon conjugation to a polymer, peptide or monoclonal antibody (MAb). Numerous articles have described methods of drug conjugation that seek to preserve drug activity while forming a stable bio-conjugate. Unfortunately many drug-carrier conjugates also dissociate when subjected to the challenge of an in vivo serum environment. Moreover, tumor uptake of the drug is often reduced while non-specific toxicity to normal tissues is often increased.

An advanced method for delivering a drug to a disease site in a less toxic and more efficient and efficacious manner, is the use of antibody-directed enzyme prodrug therapy (ADEPT). See, for example, U.S. Pat. No. 5,632,990 (Bagshawe). Originally, ADEPT depended on the use of a conjugate of an antibody and an enzyme to localize the latter to a site of disease. Such an approach had several drawbacks, including loss of antibody and/or enzyme activity upon conjugation, and high residual levels of circulating MAb enzyme conjugate in the bloodstream due to the long-circulating MAb. The latter, in turn, resulted in excessive enzyme activity in circulation upon administration of the prodrug, which was cleaved by enzyme in the bloodstream, generating high levels of active drug, and high levels of non-specific drug toxicity.

Later, the use of bispecific antibodies (bsAbs) was suggested for application to the ADEPT method. In this approach, a bispecific antibody targeting both a disease-associated antigen with one arm, and an epitope on an enzyme with a second arm would be given to a subject, followed some time later by the enzyme in question, and finally by the prodrug that the enzyme was active against. This comprises a three-step delivery system, absent any clearing agents. Difficulties encountered in the practice of this ADEPT method in the second capture step, that is by the second arm of the bsAb against the enzyme epitope, perhaps due to low affinity of this antibody-antigen complex, led to protocols where the bsAb and the enzyme were mixed together, and administered as a single complex, followed later by the prodrug. This altered approach comprises a two-step delivery system, absent any clearing agents. However, this modified ADEPT method remained fraught with problems preventing its ultimate wide application in patients. These included the utility of the targeting arm of the bsAb, bsAb preparation issues, binding affinity of the second (anti-enzyme epitope) arm of the bsAb, choice of prodrug, efficiency of prodrug cleavage by the enzyme, and, not least, presence of active enzyme in non-target tissues at the time of prodrug administration. The latter leads to unwanted cleavage of prodrug in normal tissues, and, subsequently, untoward toxicity due to the generation of active drug in those tissues. A particular problem was encountered in the cleavage of prodrug to drug in the circulation by active enzyme.

A continuing need therefore exists for methods and compositions that are able to selectively deliver therapy agents to a disease site using an ADEPT approach, without undue dissociation of bsAb and enzyme, and without adversely affecting a therapeutic agent's potency.

SUMMARY OF THE INVENTION

The inventors have surprisingly discovered that when a multispecific targeting protein (e.g., a bispecific monoclonal antibody or bispecific antibody fragment) is pre-mixed with a hapten-enzyme covalent conjugate, the resulting complex can be used to localize the enzyme specifically to the site of disease via the targeting arm of the multispecific antibody. The strength of complex binding between the secondary

[hapten-binding] arm of the multispecific antibody and the hapten-enzyme conjugate is sufficient to hold the enzyme in a position and concentration suitable for successful ADEPT. The non-covalently bound complex of bsAb/hapten-enzyme remains in circulation for an extended period, showing the stability of the binding between the hapten-binding arm of the bsAb and the hapten-enzyme conjugate. Because the secondary arm of the bsAb is raised against a carefully selected hapten, rather than a non-defined epitope on a particular enzyme, the secondary arm of the bsAb can be carefully screened to have the optimum binding properties. In addition, the same secondary arm-containing bsAb may be used with different enzymes, since the same recognition hapten is being recognized, once the hapten is substituted onto a different enzyme. Such a non-covalently bound complex represents an example of a superior general method for delivery of therapy agents, using ADEPT, to disease tissue targets. This new ADEPT methodology can be adopted to circumvent the aforementioned problems with covalent drug-carrier conjugates, as well as problems seen with earlier versions of the ADEPT concept.

In one aspect, the invention relates to a method for treating target cells, tissues or pathogens in a subject, such as a mammal, comprising administering in sequence:

a therapeutically effective amount of a non-covalently bound complex to said subject thereby forming a target-tissue-localized complex;

wherein said non-covalently bound complex comprises a multispecific targeting protein comprising at least one target-binding site and one hapten-binding site, and a hapten-enzyme covalent conjugate;

wherein said at least one target-binding site is capable of binding to at least one complementary binding moiety on the target cells, tissues or pathogens or on a molecule produced by or associated with said target cells, tissues or pathogens; and wherein said hapten-binding site is non-covalently bound to the hapten-enzyme covalent conjugate;

optionally, a clearing agent; and a chemotherapeutic drug or prodrug, capable of being converted to an active drug by the target-tissue-localized complex. More specifically, the chemotherapeutic drug is converted to an active drug by a target-tissue-localized complex that comprises an enzyme.

In another aspect, the invention relates to a kit comprising, in separate containers:

a multispecific targeting protein, comprising at least one target-binding site and a hapten-binding site, pre-mixed with a hapten-enzyme conjugate; and a chemotherapeutic pro drug.

In yet another aspect, the invention relates to a kit comprising, in separate, suitable containers:

a multispecific targeting protein, comprising at least one target-binding site and a hapten-binding site;

a hapten-enzyme conjugate; and a chemotherapeutic pro drug;

wherein said multispecific targeting protein, comprising at least one target-binding site and a hapten-binding site and said hapten-enzyme conjugate are mixed immediately prior to use.

In yet another aspect, the invention relates to a method of making a stable non-covalently bound complex that is capable of localizing to a target cell, tissue, or pathogen comprising admixing a multispecific targeting protein comprising at least one target-binding site and a hapten-binding site, and a hapten-enzyme covalent conjugate;

wherein said at least one target-binding site is capable of binding to at least one complementary binding moiety on said target cells, tissues or pathogens or on a molecule produced by or associated with said target cells, tissues or pathogens; and wherein said hapten-binding site is capable of stably and non-covalently binding said hapten-enzyme conjugate; thereby making a stable non-covalently bound complex.

In still another aspect, the invention relates to a method of treating a subject, comprising administering a therapeutically effective amount of a non-covalently bound complex, said non-covalently bound complex resulting from the pre-mixing of said multispecific targeting protein and a hapten-enzyme conjugate, prior to administration to said subject.

DETAILED DESCRIPTION

As used herein, the term "subject" refers to any mammal. In one embodiment, the mammal is a human.

Non-Covalently Bound Complex: A Multispecific Targeting Protein and a Hapten-Enzyme Conjugate.

As used herein, the term "targeting protein" is a multispecific binding protein, such as a bispecific antibody, or a recombinantly produced antigen-binding molecule in which two or more of the same or different natural antibody, single-chain antibody or antibody fragment segments with different specificities are linked. The valency of the targeting protein refers to the total number of binding arms or sites the targeting protein has to an antigen or epitope. Thus, depending on the total number of binding arms or sites the targeting protein has to an antigen or epitope, the targeting protein may be monovalent, bivalent, trivalent or multivalent. A multivalent targeting protein has the advantage of multiple interactions in binding to an antigen, thus increasing the avidity of binding to said antigen.

The specificity of the targeting protein refers to how many antigens or epitopes a targeting protein is able to bind. Thus, the targeting protein may be monospecific, bispecific, trispecific or multispecific. A multispecific targeting protein has the advantage of multiple interactions in binding to separate antigens, thus increasing the avidity of binding to the cellular target. Using these definitions, a natural antibody (e.g., an IgG) is bivalent because it has two binding arms but is monospecific because it binds to one antigen.

Monospecific (to target cell), multivalent targeting proteins have more than one binding site for an epitope, but only bind with the same epitope on the same antigen. A second example of a monospecific, multivalent targeting protein is a diabody with two binding sites reactive to the same antigen. The targeting protein may comprise both multivalent and multispecific combinations of different antibody components including multiple copies of the same antibody components.

Examples of multivalent target binding proteins are described in Patent Appl. Ser. No. 60/220,782. Multivalent target binding proteins have been made by cross-linking several Fab-like fragments via chemical linkers. See U.S. Pat. Nos. 5,262,524; 5,091,542 and Landsdorp et al. *Euro. J. Immunol.* 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al. *Protein Engineering* 10(4): 423-433 (1997).

In a preferred aspect of the invention, the multivalent and multispecific targeting protein is a bispecific antibody. Such a targeting protein is exemplified by a Fab'×Fab' fragment, wherein the first Fab' fragment binds to an anti-tumor cell epitope, and the second Fab' fragment binds to a low molecular weight hapten. In this embodiment the two distinct specificity Fab' fragments can be linked through their hinge region thiol groups using commercially available cross-linkers and methods well-known in the art. A second targeting protein is exemplified by a F(ab')$_2$×Fab' fragment, wherein the divalent F(ab')$_2$ fragment binds to an anti-tumor cell epitope, and the monovalent Fab' fragment binds to a low molecular weight hapten. Similarly, a third targeting protein is exemplified by an intact IgG×Fab' fragment, wherein the divalent IgG binds to an anti-tumor cell epitope, and the monovalent Fab' fragment binds to a low molecular weight hapten. Other combinations of specificity and valency of both the anti-target cell arm and the anti-hapten arm may be readily envisaged.

In one preferred aspect of the invention, the multivalent and multispecific (to cellular target and to hapten) targeting protein is a bivalent anti-antigen and monovalent anti-hapten bispecific antibody. Bivalency toward the cellular target better retains the ability of the composition to remain on the cell surface, or associated with the cell for an extended period of time. Monovalency to the hapten limits the amount of cross-linking that can take place with a hapten-enzyme conjugate, and therefore regulates final molecular size. A specific example of such an agent is an anti-CEA×anti-indium-DTPA F(ab')$_2$×Fab' bispecific antibody, wherein CEA refers to carcinoembryonic antigen and DTPA refers to diethylenetriaminepentaacetic acid. Further examples will be discussed below.

The target-binding site of a disease-targeting antibody arm is capable of binding to a complementary binding moiety on the target cells, tissues, pathogens or on a molecule produced by, or associated with, the target cell tissue or pathogen. In a preferred aspect of the present invention, the pathogen is selected from the group consisting of a virus, a fungus, a parasite and a bacterium. The complementary binding moieties that are contemplated in one aspect of the present invention include, but are not limited to tumor-associated antigens (TAAs), wherein said antigens are selected from the group consisting of AFP (alpha fetal protein), carbonic anhydrase IX, A3, antigen specific for A33 antibody, BrE3-antigen, CD1, CD1a, CD3, CD5, CD15, CD16, CD19, CD20, CD21, CD22, CD23, CD25, CD30, CD37, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, folate receptor, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, MUC16, PAM- 4-antigen, PSA, PSMA, RS5, S100, TAG-72, p53, tenascin, IL-2, IL-6, IL-8, insulin growth factor-1 (IGF-1), T101, Tn antigen, Thomson-Friedenreich antigens, tumor necrosis antigens, VEGF, placenta growth factor (P1GF), 17-1A-antigen, an angiogenesis marker, ED-B fibronectin, an oncogene marker, bcl-2, an oncogene product, and other tumor-associated antigens. Recent reports on tumor associated antigens include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63), each incorporated herein by reference. Specific targeting antibodies of use include, but are not limited to: MN-14 (anti-carcinoembryonic antigen), Mu-9 (anti-colon specific antigen-P), LL2 (anti-CD22), LL1 (anti-CD74), hA20 (anti-CD20) and RS7 (anti-epithelial glycoprotein). Such antibodies encompass chimeric, humanized and human antibodies containing the same CDRs as their corresponding murine antibodies. See U.S. Pat. Nos. 5,874,540; 5,789,554 and 6,187,287. See also pending U.S. patent application Ser. Nos. 10/116,116 (now issued U.S. Pat. No. 7,387,772); 09/337,756 (now U.S. Pat. No. 7,074,405); 60/360,259; and 60/356,132.

The multispecific targeting protein also has an arm referred to as the hapten-binding site or arm. The hapten-binding site is typically an antibody or a hapten-binding antibody fragment and is raised against a defined, low molecular weight hapten. Such low molecular weight haptens include agents such as DTPA (diethylenetriaminepentaacetic acid), DOTA (1,4,7,10-tetraazacyclododecane-N,N',N'',N'''-tetraacetic acid) and HSG (histamine succinyl glycine moiety):

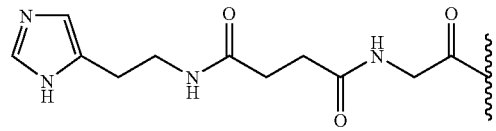

The antibodies are generally raised after binding of the low molecular weight hapten to an immunogen (e.g., keyhole limpet hemocyanin, or another foreign protein) using methods well know in the art. Specific examples of antibodies that can comprise the hapten-binding site of a multispecific targeting protein include MAbs 734 (anti-diethylenetriaminepentaacetic acid-indium complex; anti-DTPA), 679 (anti-histaminyl succinyl glycyl; anti-HSG) and LG1 (anti-DOTA).

Aside from the MAbs disclosed herein, it can be appreciated that other MAbs can be raised to any hapten or drug by standard methods of making MAbs known to a person skilled in the art. For instance, it is possible to attach a hapten such as HSG to an immunogenic stimulator or adjuvant such a keyhole limpet hemocyanin, and inject the conjugate into immunocompetent animals. Multiple injections are often employed. It must be appreciated that such an approach can lead to several different antibodies with slightly different specificities against the hapten in question, such as HSG. MAbs can recognize different sub-parts of the HSG structure, or different conformations. MAbs may also be obtained that recognize a little more than just the HSG molecule itself, such as recognizing an HSG moiety only when attached to an epsilon amino group of lysine, if indeed, the HSG was initially linked to the KLH (for example) by attachment to an epsilon lysyl amino group on the latter immunogenic protein. Without wishing to be exhaustive, these general procedures and results are well known in the art. It is also then well known art for the isolation of spleen cells producing antibodies from these immunized animals, and their subsequent fusion with myeloma cell lines, to generate hybridomas secreting anti-hapten antibodies. See Kohler G. and Milstein C., *Eur. J. Immunol.* 6:511-9 (1976); Kohler G. et al., *Eur. J. Immunol.* 6:292-5 (1976); Harlowe and Lane, 1988, *Antibodies: A Laboratory Manual*, Cold Spring Harbor Laboratory; and Kohler G. and Milstein C. *Nature* 256:495-7 (1975).

Multispecific targeting proteins can be prepared chemically from antibodies that have differing specificity by well-known reactions. Typically, one MAb is activated by reaction with a cross-linking agent, with the latter chosen to react at the first MAb's lysine, reduced cysteine, or oxidized carbohydrate residues. After purification, the activated first MAb is mixed with the second MAb, which then reacts specifically with a second functionality of the original cross-linking agent; most notably via the second MAb's lysine, reduced cysteine or oxidized carbohydrate residues. Multispecific targeting proteins can also be prepared somatically by the quadroma technique. The quadroma technique is a technique wherein a cell line expressing both arms of the bispecific antibody is produced and grown in culture to secrete the bsMAb. Finally, bsMAbs can also be produced conveniently by modern techniques of molecular biology. See, for example Colman, A., Biochem. Soc. Symp. 63: 141-147 (1998); U.S. Pat. No. 5,827,690; and Published U.S. application No. 20020006379, now U.S. Pat. No. 6,962,702.

BsAbs of the types exemplified above can be pre-mixed with several different hapten-enzyme conjugates to produce and deliver an effective therapeutic agent, after appropriate prodrug administration, depending on what the pertinent arm of the bsAb has been raised against. In a preferred embodiment, the enzyme contained in the hapten-enzyme covalent conjugate is selected from the group consisting of an esterase, carboxylesterase, carboxypeptidase, amidase, glucoronidase and galactosidase. Most preferably, the esterase is a carboxylesterase selected from the group consisting of rat, mouse, rabbit, porcine and human carboxylesterase. The enzyme may be produced by recombinant techniques well known in the art (Wolfe, et al. 1999). The enzyme may be produced in yeast, bacteria, plants, insect or animal cells. Preferably, the enzyme has been modified to enhance its catalytic properties (Wolfe et al, 1999). The modification may be performed via site-directed mutagenesis. See U.S. Pat. Nos. 5,352,594 and 5,912,161 for a general discussion of site-directed mutagenesis. In any case, the desired effect of the mutagenesis is to reduce the Michaelis constant of the enzyme, enabling more efficient enzyme activity at lower concentrations of prodrug substrate. It is preferred that the multispecific targeting protein binds to both its antigenic target and to its hapten target via the target binding site and the hapten-binding site, respectively, with a dissociation constant of about $10^{-7}$; more preferably about $10^{-9}$.

Haptens can be attached to enzymes in several ways. For instance, the DTPA hapten can be coupled to the enzyme carboxylesterase at certain individual positions on the enzyme to give the hapten-enzyme covalent conjugate. Most simply the commercially available precursor DTPA dianhydride is added to a solution of enzyme in an appropriate buffer, at pH 7-9. After a reaction of from 1-16 hours, using an appropriate molar excess of DTPA-dianhydride, one or more units of DTPA are attached to the enzyme, by reaction of the latter's lysyl residues with one anhydride group of the precursor. The DTPA-enzyme conjugate is separated from unreacted, hydrolyzed DTPA and buffer components by standard methods for effecting such separations, such as ammonium sulfate precipitation, diafiltration or size-exclusion or ion-exchange chromatography. To obtain the bsAb-hapten-enzyme conjugate the hapten-enzyme covalent conjugate is then mixed with a bsAb, such as MN-14×734 bsAb (anti-CEA×anti-DTPA) to give a non-covalently bound complex wherein the target-binding site capable of binding to a complementary binding moiety on the target cells is MN-14. A typical complex might then be: MN-14×734 bsAb/DTPA-carboxylesterase. The bsAb and the hapten-enzyme conjugate may be mixed together in ratios of from 5:1 to 1:5, or more preferably in ratios of from 2:1 to 1:2. However, these ratios are not limiting and other ratios, for example 5:1, 4:1, 3:1, 2:1, 1:1, 1:2, 1:3, 1:4 or 1:5, or any range in between any of these ratios, may be utilized. The complex may be made immediately prior to use, or it may be made in advance and stored under appropriate conditions until required. It may also be frozen for shipping and future use, or formulated for long-term storage by lyophilization. Such methods are well known in the art.

The hapten-enzyme conjugate may also be made using an alternate approach, designed to attach two hapten recognition units to the enzyme in one chemical reaction. In this approach, an intermediate comprising two such hapten recognition units is attached to a short peptide carrier backbone that also incorporates a group for activation and coupling to the enzyme. The agent has the general formula: X-peptide(-X)-(reactive group); where the peptide is 2-10 amino acid residues in length, preferably 2-5 amino acid residues in length, most preferably, the peptide is 3-4 amino acid residues in length. The X moieties are recognition hapten residues mentioned previously, exemplified by In-DTPA, DOTA or HSG sub-units; and the reactive moiety comprises a functionality that can be coupled to the enzyme without interference from the rest of the bivalent recognition conjugate. An Example of such a structure is Ac-NH-Lys(HSG)-Tyr-Lys (HSG)-COOH; a tripeptide of two lysyl residues and one tyrosyl residue, linked together by amide bonds, and blocked on its alpha amino group by an unreactive group such as an acetyl residue. The amino acids may be in the L- or the D-conformation. Each lysyl residue, though its epsilon amino group, is attached to an HSG recognition unit. The reactive moiety in this instance is a carboxyl group that can be further activated via an anhydride, active ester or other such activating agent, for coupling to free amino groups on an enzyme.

A second similar example of such a structure is 4(4-N-maleimidomethyl)cyclohexanecarboxyamido-Lys(DTPA)-Tyr-Lys(DTPA)-$CONH_2$; a tripeptide of two lysyl residues and one tyrosyl residue, linked together by amide bonds, and blocked on its carboxyl terminal group by an unreactive group such as an amide residue. The amino acids may be in the L- or the D-conformation. Each lysyl residue is attached to a DTPA recognition unit. The reactive moiety in this instance is a maleimido group that might be coupled to free thiol groups on an enzyme, wherein the free thiol groups are present endogenously, or are placed there by prior reaction of the enzyme with a thiolating agent such as Traut's reagent.

Many more such compositions can be envisaged as useful within the context of the current invention. See for example published U.S. application No. 20020006379, now U.S. Pat. No. 6,962,702, and pending U.S. application Ser. No. 09/337, 756, now U.S. Pat. No. 7,074,405, each incorporated herein by reference in their entirety.

After administration, localization to the site of disease, and substantial clearance from normal tissues of the bsAb/hapten-enzyme complex, a drug or prodrug substrate to the enzyme in question may be given. For example, with a CEA-expressing tumor, the above MN-14×734 bsAb, pre-complexed with DTPA-carboxylesterase is given, allowed to localize to CEA-expressing tumor sites, and clear normal tissues, before the prodrug CPT-11 (irinotecan) (a substrate for carboxylesterase) is given. The non-covalently bound bsAb-hapten-enzyme complex that has localized at the tumor, activates the subsequently administered prodrug specifically at the site of the tumor. A variety of chemotherapeutic agents or prodrugs of chemotherapeutic agents may be used in the practice of the preferred embodiments of the present invention for treatment of subjects. Such chemotherapeutic agents include, but are not limited to, adriamycin, actinomycin, calicheamycin, epothilones, maytansine, mitomycin, carminomycin, daunomycin, doxorubicin, tamoxifen, taxol and other taxanes, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s), neomycin, and podophyllotoxin(s). Anti-metabolites such as cytosine arabinoside, amethopterin; anthracyclines; vinca alkaloids and other alkaloids; antibiotics, demecolcine; etopside; mithramycin; and other anti-tumor alkylating agents are also contemplated for use in the present invention.

Preferred prodrugs of the preferred embodiments are those derived from the drugs selected from the group consisting of camptothecin, doxorubicin, taxol, actinomycin, maytansine, calicheamycin and epothilones.

The term "prodrug" refers to an agent that is converted into the parent drug in vivo. Prodrugs are often useful because, in some situations, they may be easier to administer than the parent drug. The prodrug, for instance, may be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. *Progress in Drug Research* 4:221-294 (1962); Morozowich et al., "Application of Physical Organic Principles to Prodrug Design" in E. B. Roche ed. *Design of Biopharmaceutical Properties through Prodrugs and Analogs*, APHA Acad. Pharm. Sci. (1977); *Bioreversible Carriers in Drug in Drug Design*, Theory and Application, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenyloin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Adv. Drug Delivery Rev.* 8(1): 1-38 (1992); Fleisher et al. "Improved oral drug delivery: solubility limitations overcome by the use of prodrugs", *Adv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *J. Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *J. Chem. Soc., Chem. Commun.*, 875-877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", *Eur. J. Pharm. Sci.* 4: 49-59 (1996); Gangway et al., "Pro-drug, molecular structure and percutaneous delivery", *Des. Biopharm. Prop. Prodrugs Analogs, [Symp. J* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HW nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989).

A clearing agent may be optionally added after administration of the noncovalently bound multispecific antibody-hapten-enzyme complex to a subject. The clearing agent is preferably an antibody directed against an epitope of the multispecific targeting protein/hapten-enzyme complex. Most preferably, the clearing agent is an anti-idiotic antibody, a carbohydrate-derivatized anti-idiotic antibody or a galactosylated anti-idiotypic antibody to the multispecific targeting protein.

Non-proteinaceous polymers can also serve as the backbone onto which other drugs or prodrugs useful in the present invention may be attached. The polymeric material serves to detoxify and solubilize the active drug. For instance a co-polymer consisting of (Lys)m (Glu)n(Taxol)$_y$ (wherein m is an integer from 10-500, n is an integer from 10-500, and y is an integer from 1-50 (SEQ ID NO: 1)) can be applied in this manner, being given after the injection, localization and clearance of the multispecific antibody-hapten-enzyme complex. In this instance, the enzyme in question would comprise an esterase, capable of cleaving the ester bond between taxol and the gamma-carboxyl groups of the multi-glutamic acid units. This type of prodrug is based on the utility of polymeric material to carry active drugs in circulation for an extended period of time. See Auzenne et al., *Clin Cancer Res.* 8: 573 (2002) and Li et al., Cancer Res., 1998. Other drugs, such as camptothecins may be used in a similar manner, and other polymers such as poly-N-(2-hydroxypropyl)methacrylamide (HPMA) may also be applied as carriers. The invention also contemplates the incorporation of unnatural amino acids, e.g., D-amino acids, into the non-proteinaceous polymers. The invention further contemplates other backbone structures such as those constructed from non-natural amino acids. See for example, published U.S. application No. 20030026764, now abandoned.

In another aspect, the invention relates to a method of making a stable target-tissue-localized complex comprising pre-mixing a multispecific targeting protein comprising at least one target-binding site and a hapten-binding site, and a hapten-enzyme covalent conjugate;

wherein said at least one target-binding site is capable of binding to at least one complementary binding moiety on the target cells, tissues or pathogens or on a molecule produced by or associated with said target cells, tissues or pathogens; and wherein said hapten-binding site is capable of stably and non-covalently binding a hapten-enzyme conjugate; thereby forming a stable target-tissue-localized complex.

Formulations and Kits

The multispecific targeting protein and hapten-enzyme covalent conjugate that comprises the non-covalently bound complex preferably also comprise a pharmaceutically acceptable carrier or excipient. A pharmaceutically acceptable carrier is a carrier or diluent that does not cause significant irritation to an organism and does not abrogate the biological activity and properties of the administered compound. An excipient is an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycol derivatives.

One aspect of the present invention relates to a kit comprising, in suitable containers, separate or together:

a multispecific targeting protein, comprising a target tissue-binding site and an hapten-binding site, pre-mixed with a hapten-enzyme conjugate; and a chemotherapeutic pro drug.

Another aspect of the invention relates to a kit comprising, in separate, suitable containers:

a multispecific targeting protein, comprising at least one target-binding site and a hapten-binding site;

a hapten-enzyme conjugate; and a chemotherapeutic pro drug;

wherein said multispecific targeting protein, comprising at least one target-binding site and a hapten-binding site and said hapten-enzyme conjugate are mixed immediately prior to use.

The kit, may comprise the non-covalently bound complex and a pharmaceutically acceptable carrier or excipient. Likewise, the kit may comprise the prodrug in a pharmaceutically acceptable carrier or excipient. In a preferred embodiment of the present invention, the kit comprises a bispecific antibody such as anti-CEA×anti-indium-DTPA-F(ab')$_2$. The bispecific antibody is mixed with an equimolar amount of the enzyme-hapten conjugate DTPA-carboxylesterase. The kit can contain from about 1-10,000 mg of the mixture. The kit can be stored as a sterile solution, frozen at −20 to −80° C., or it can be lyophilized to powder form for long-term storage. In one embodiment, these formulations could include a preformed single vial kit comprising multispecific antibody-hapten-enzyme conjugate, or two separate vials containing multispecific antibody, and hapten-enzyme, respectively, which are then mixed prior to administration. From a formulation and stability perspective, the hapten-enzyme may be kept separate for long-term storage, and these determinations need to be made empirically, for each individual application of the technology.

Dosage

An amount of the non-covalently bound complex necessary for treating target cells, tissues or pathogens in a subject when provided to a subject is a "therapeutically effective" amount. In order to treat the target cells, tissues or pathogens, it is desirable to provide from about 0.001 to about 10,000 micromoles of non-covalently bound complex per kilogram of subject weight. This dosage may be administered over a period from about 1 minute to about 4 hours, by any suitable means, but prior to the administration of the chemotherapeutic drug or prodrug. The non-covalently bound complex of the present invention may be dissolved in any physiologically tolerated liquid in order to prepare an administrable amount. It is preferable to prepare such a solution of the non-covalently bound complex by dissolving the non-covalently bound complex in normal saline, phosphate buffered saline (pH from about 5 to about 8), acetate buffered saline (pH from about 4 to about 7), phosphate buffer (pH from about 5 to about 8), or acetate buffer (pH from about 4 to about 7). Buffered concentrations in the 0.02 to 2 molar range are acceptable.

An amount of the chemotherapeutic drug or prodrug necessary to treat target cells, tissues or pathogens in a subject when provided after the administration of the non-covalently bound complex to a subject is a "therapeutically effective" amount. In order to treat the target cells, tissues or pathogens, it is desirable to provide from about 0.001 to about 10,000 μmol of non-covalently bound complex per kilogram of subject weight. This dosage may be administered over a period from about 1 minute to about 4 hours, by any suitable means, but following the administration of the non-covalently bound complex. The chemotherapeutic drug or prodrug of the preferred aspects of the present invention may be dissolved in any physiologically tolerated liquid in order to prepare an administrable amount. It is preferable to prepare such a solution of the non-covalently bound complex by dissolving the non-covalently bound complex in normal saline, phosphate buffered saline (pH from about 5 to about 8), acetate buffered saline (pH from about 4 to about 7), phosphate buffer (pH from about 5 to about 8), or acetate buffer (pH from about 4 to about 7). Buffered concentrations in the 0.02 to 2 molar range are acceptable. Drugs or prodrugs may be administered in the ways that they are usually administered when given as independent active entities. For instance, hydrophobic drugs or prodrugs may be given in dextrose solutions or as admixtures with cremophor.

Suitable routes of administration of the non-covalently bound complex and the chemotherapeutic drug or prodrug include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are parenteral. Alternatively, one may administer the bsAb/enzyme-hapten complex and the drug or prodrug in a local rather than systemic manner, for example, via injection of the compound directly into a solid tumor.

The ordinary skilled artisan will appreciate that the pre-mixing of the multispecific targeting protein and the hapten-enzyme conjugate, prior to administration to a subject, can be done with immediately before administration, or, it can be done well in advance.

Treatment

In another aspect, the invention relates to a method of treating a subject, comprising administering a therapeutically effective amount of a non-covalently bound complex, said non-covalently bound complex resulting from the pre-mixing of said multispecific targeting protein and a hapten-enzyme conjugate, prior to administration to a subject.

Diseases that may be treated using the pre-mixed multispecific targeting proteins and hapten-enzyme conjugates of the preferred embodiments of the present invention include, but are not limited to malignancies. These may include all solid and non-solid tumor cancers. In the case of the latter, B-cell cancers, or T-cell cancers can be treated (e.g., non-Hodgkins lymphoma, T-cell lymphoma or chronic lymphocytic leukemia). Equally, solid tumors may be treated using the current compositions and methods. These include, but are not limited to, adenocarcinomas and sarcomas. Major cancers of endodermally-derived digestive system epithelia, and cancers of the breast, prostate and lung are contemplated and treatable using this approach. In preferred applications diseases expressing antigens such as AFP (alpha fetal protein), HCG (human chorionic gonadotropin), EGP-1, EGP-2, CD37, CD74, colon-specific antigen-p (CSAp), carcinoembryonic antigen (CEA), CD19, CD20, CD21, CD22, CD23, CD30, CD74, CD80, HLA-DR, Ia, MUC 1, MUC 2, MUC 3, MUC 4, EGFR, HER 2/neu, PAM-4, TAG-72, EGP-1, EGP-2, A3, KS-1, Le(y), S100, PSMA, PSA, tenascin, folate receptor, VEGF, necrosis antigens, IL-2, T101 and MAGE can be targeted with an appropriate antigen-targeting antibody arm on the multispecific antibody. Specific targeting antibodies include, but are not limited to: MN-14 (anti-carcinoembryonic antigen), Mu-9 (anti-colon specific antigen-P), LL2 (anti-CD22), LL1 (anti-CD74), hA20 (anti-CD20) RS7 (anti-epithelial glycoprotein-1). Such antibodies encompass chimeric, humanized and human antibodies containing the same CDRs as their corresponding murine antibodies.

Other diseases than cancer can also be targeted using these multispecific antibody/hapten-enzyme conjugates. For example, anti-CD19, anti-CD20, anti-CD22 and anti-CD74 antibodies can be used to treat immune dysregulation diseases and related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangiitis obliterans, (repeat), primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

The following examples are meant to be illustrative of the methods, compositions and uses of the invention, and are not intended to be limitative.

EXAMPLE 1

Preparation of a Carboxylesterase-DTPA Conjugate

Two vials of rabbit liver carboxylesterase (about 8.5 mg protein content/vial) are reconstituted with 2.3 mL of 50 mM potassium phosphate buffer pH 7.5, and the solution is made 4.2 mM in DTPA using 0.1 mL of a 0.1 M stock solution of DTPA pH 6.7. The pH of the resultant solution is adjusted to be in the 7.7-7.8 range, and then reacted with 10 mg of cyclic DTPA dianhydride. After 1 h of stirring at the room temperature, the reaction mixture is passed through two successive SEC columns equilibrated in 0.1 M sodium phosphate pH 7.3. The eluate is further purified by preparative HPLC on a TSK G3000SW column using 0.2 M sodium phosphate pH 6.8, at 4 mL/min flow, as the eluent. The purified conjugate is made 0.1 M in sodium phosphate pH 6.8, and concentrated. The DTPA-to-carboxylesterase molar substitution ratio, determined by a metal-binding assay, is estimated to be in the range of 2.95-to-1 to 4.43-to-1.

Preparation of hMN-14 IgG×734 Fab' Bispecific Antibody

HMN-14 IgG (8.45 mg, MW 150K) was derivatized with a 1.8-fold molar excess of sulfo-SMCC, at pH 7.21, for 45 minutes at ambient temperature. The product was purified by centrifuged SE column ('spin column') of Sephadex G50/80 in 0.1 M sodium phosphate, pH 6.5. The maleimide content was determined to be 0.93 moles per mole of IgG, by reacting with a known excess of 2-mercaptoethanol, followed by the determination of unused thiol by Ellman's assay. Separately, 734 F(ab')$_2$ was reduced with 0.1 M cysteine (~100-fold molar excess of cysteine) in 20 mM Hepes buffer-150 mM sodium chloride-10 mM EDTA, pH 7.3. The reduction was carried out for 50 min at 37° C. (bath) under argon flush. The reduced material was purified by two successive spin columns on Sephadex G50/80 in 0.1 M sodium phosphate-S mM EDTA, pH 6.5. The hMN-14-maleimide was reacted with 2-fold excess of 734 Fab', and incubated at ambient temperature for 1 h. The conjugate was then reacted with a 40-fold molar excess of N-ethylmaleimide for 40 min. The material was subjected to preliminary purification on spin column of Sephadex G50/80 in 0.1 M sodium phosphate, pH 7.3. The eluate from this purification was applied to a column of 3 mL of DTPA-Affigel, which was sequentially eluted with 0.2 M sodium phosphate pH 6.8 and 0.1 M EDTA, pH 3.8. Pooled EDTA fractions were dialyzed against 0.2 M sodium phosphate pH 6.8, with 2 buffer changes. The sample was applied to a preparative SE HPLC column (TSK G3000SW), with 0.2 M sodium phosphate pH 6.8 at 4 mL/min as running buffer. The major product was separated, and was found pure by SE HPLC (ret. time 9.58 min on analytical SE HPLC, 0.2 M sodium phosphate at 1 mL/min flow). Recovery: 7.69 mg. MW by MALDI mass spectral analysis was 196, 803.

EXAMPLE 2

Biodistribution of a Pre-Mixed Complex Comprising an Indium-Labeled Carboxylesterase-DTPA Conjugate and the bsMAb hMN-14×734 (IgG×Fab')

This example demonstrates the biodistribution of a pre-mixed complex of hMN-14×734 Fab' (hMN-14 is a humanized antibody of MN-14 (carcinoembryonic antigen; anti-CEA), and an indium-DTPA-carboxylesterase conjugate. Carboxylesterase-DTPA is radiolabeled for tagging purposes with indium-111 radionuclide, using commercially available In-111 acetate. Briefly, In-111 chloride was buffered with 3-times the volume of 0.5 M sodium acetate, pH 6.1; 0.12 mg of CE-DTPA was mixed with 0.25 mCi of In-111 acetate, and incubated for 40 minutes. Then added –0.01 mL of cold indium acetate [In acetate: prepared from 0.005 mL of 1.97× $10^{-2}$ M indium chloride, 0.045 mL of water and 0.15 mL of 0.5 M sodium acetate, pH 6.1.] After 20 minutes, the solution was made 10 mM in EDTA, incubated for 10 min. ITLC analyses showed 98% of radioactivity associated with carboxylesterase. The pre-mixed hMN-14×734 Fab'/In-1'-In-DTPA-carboxylesterase complex is administered to hamsters and nude mice bearing GW-39 human tumor xenografts.

Tables 1-6 show that the binding between of the carboxylesterase-DTPA conjugate and the corresponding bispecific antibody is stable in vivo, and that the In-111/In-DTPA-carboxylesterase conjugate can be effectively localized and retained at the tumor sites by its complexation with the hMN-14×734 (IgG×Fab') bsAb.

EXAMPLE 3

ADEPT Therapy Using a Pre-Mixed Complex Comprising an Indium (In)-DTPA Carboxylesterase conjugate and the bsMAb hMN-14×734 (IgG×Fab')

Male hamsters (body weight: ~75 g) are given GW-39 human tumor xenografts by injection of a 20% v/v GW-39 tumor cell suspension intramuscularly on the animals' right thigh. After 3 days, a 2:1 premixed complex of mMN-14 F(ab)$_2$×m734Fab' and Indium-DTPA-carboxylesterase, at a dose of 0.75 mg of bsAb, corresponding to 200 enzyme units per kg body weight, is administered. Five days post-injection of bsAb/In-DTPA-carboxylesterase, a maximum tolerated dose (8 mg/75 g body weight; determined earlier) of the pro drug, CPT-11, is given. A positive control group is given CPT-11 alone and an untreated group are also included in the study. Tumor growth in untreated animals is out of control at 3-4 weeks post-implantation of tumor cells, and animals are sacrificed for humane reasons. Mean tumor volumes are similar for the bsAb/In-DTPA-carboxylesterase and the positive control (CPT-11 alone) at 5 weeks, and out to 9 weeks post-implantation of tumor cells. However, the bsAb/In-DTPA-carboxylesterase treated group continues to show growth inhibition over the next five weeks, while the mean tumor volumes for the group given CPT-11 alone increase during the same period. The relative mean tumor volume for the bsAb/In-DTPA-carboxylesterase treated group at week 14 is similar to the mean tumor volume at week 9 for the positive control, CPT-11-alone-treated animals. This demonstrates a 5-week advantage in tumor growth control when applying an ADEPT approach using bsAb/In-DTPA-carboxylesterase pretargeting.

EXAMPLE 4

Preparation of Carboxylesterase-IMP222 ("CE-IMP222")

IMP222 is a di-DTPA-containing peptide with the cysteine thiol available for conjugation to maleimide-appended carboxylesterase. IMP222: Ac-Cys-Lys(DTPA)-Tyr-Lys(DTPA)-$NH_2$ (SEQ ID NO: 2). Carboxylesterase (0.0245 umol) was derivatized with a 17.5-fold molar excess of sulfo-SMCC [sulfosuccinimidyl 4(N-maleimidomethyl)-1-cycclohexane carboxylate] in 0.1 M sodium phosphate, pH 7.3, at the ambient temperature for 45 minutes. The product was purified on a 2-mL centrifuged SE column ('spin column') of Sephadex G50/80 in 0.1 M sodium phosphate, pH 7.3. The solution of the product was made 1 mM in EDTA, and reacted with a 20-fold molar excess of IMP-222 contained in 0.1 M sodium phosphate-5 mM EDTA, pH 6.5, for 45 minutes at the ambient temperature. The product was purified by 'spin column' of Sephadex G50/80 in 0.1 M sodium phosphate, pH 7.3. Metal binding analysis using excess of indium acetate spiked with radioactive indium, gave an average of 4.5 DTPAs/conjugate in two determinations, or average of 2.25 IMP222 moieties per conjugate. Test labeling with In-111 acetate gave 94% incorporation as assayed by ITLC. The material was completely complexed by mixing with a 5-fold molar excess of F6x734 Fab' Fab' bispecific antibody, as judged by the shift of the HPLC peak to the higher MW region of the complex.

TABLE 1

Biodistributions of 2:1 pre-mixed complex of [$^{125}$I]-hMN-14 IgG × 734 Fab' [IgG × Fab'] bispecific antibody ("$^{125}$I-BsAb") and [$^{131}$I]-In-DTPA-carboxylesterase ("$^{131}$I-CE-DTPA") in hamsters bearing GW-39 human tumor xenografts

| | % Injected dose of radioactivity per gram of tissue | | | |
|---|---|---|---|---|
| Tissue | 24 h | 48 h | 120 h | 168 h |
| Tumor: | | | | |
| $^{125}$I-BsAb | 1.34 ± 0.51 | 2.79 ± 2.21 | 2.60 ± 1.55 | 1.52 ± 0.46 |
| $^{131}$I-CE-DTPA | 0.72 ± 0.40 | 1.23 ± 0.92 | 0.93 ± 0.55 | 0.55 ± 0.26 |
| Liver: | | | | |
| $^{125}$I-BsAb | 0.86 ± 0.68 | 0.40 ± 0.06 | 0.10 ± 0.03 | 0.11 ± 0.04 |
| $^{131}$I-CE-DTPA | 0.62 ± 0.52 | 0.28 ± 0.04 | 0.07 ± 0.02 | 0.06 ± 0.03 |
| Spleen: | | | | |
| $^{125}$I-BsAb | 0.66 ± 0.27 | 0.46 ± 0.12 | 0.17 ± 0.06 | 0.13 ± 0.05 |
| $^{131}$I-CE-DTPA | 0.43 ± 0.20 | 0.27 ± 0.07 | 0.13 ± 0.07 | 0.08 ± 0.03 |
| Kidney: | | | | |
| $^{125}$I-BsAb | 0.72 ± 0.47 | 0.40 ± 0.10 | 0.15 ± 0.02 | 0.16 ± 0.05 |
| $^{131}$I-CE-DTPA | 0.49 ± 0.33 | 0.24 ± 0.04 | 0.07 ± 0.02 | 0.08 ± 0.02 |
| Lungs: | | | | |
| $^{125}$I-BsAb | 5.57 ± 7.48 | 0.77 ± 0.18 | 0.16 ± 0.05 | 0.18 ± 0.06 |
| $^{131}$I-CE-DTPA | 2.59 ± 3.10 | 0.40 ± 0.12 | 0.06 ± 0.03 | 0.07 ± 0.04 |
| Blood: | | | | |
| $^{125}$I-BsAb | 2.93 ± 1.67 | 1.75 ± 0.29 | 0.37 ± 0.05 | 0.43 ± 0.11 |
| $^{131}$I-CE-DTPA | 1.86 ± 1.10 | 0.98 ± 0.21 | 0.11 ± 0.08 | 0.19 ± 0.10 |

TABLE 2

Biodistributions of 2:1 pre-mixed complex of [$^{125}$I]-MN-14 F(ab')$_2$ × 734 Fab' [F(ab')$_2$ × Fab] bispecific antibody ("$^{125}$I-BsAb") and [$^{131}$I]-In-DTPA-carboxylesterase ("$^{131}$I-CE-DTPA") in hamsters bearing GW-39 human tumor xenografts

| | % Injected dose of radioactivity per gram of tissue | | | | |
|---|---|---|---|---|---|
| Tissue | 24 h | 48 h | 72 h | 96 h | 168 h |
| Tumor: | | | | | |
| $^{125}$I-BsAb | 2.01 ± 1.20 | 2.13 ± 1.28 | 1.01 ± 0.79 | 0.98 ± 0.33 | 0.18 ± 0.05 |
| $^{131}$I-CE-DTPA | 1.07 ± 0.64 | 1.15 ± 0.75 | 0.57 ± 0.45 | 0.56 ± 0.19 | 0.13 ± 0.04 |
| Liver: | | | | | |
| $^{125}$I-BsAb | 0.18 ± 0.05 | 0.16 ± 0.03 | 0.09 ± 0.05 | 0.05 ± 0.02 | 0.02 ± 0.00 |
| $^{131}$I-CE-DTPA | 0.16 ± 0.04 | 0.15 ± 0.02 | 0.09 ± 0.04 | 0.05 ± 0.02 | 0.02 ± 0.01 |

TABLE 2-continued

Biodistributions of 2:1 pre-mixed complex of [$^{125}$I]-MN-14 F(ab')$_2$ × 734 Fab' [F(ab')$_2$ × Fab] bispecific antibody ("$^{125}$I-BsAb") and [$^{131}$I]-In-DTPA-carboxylesterase ("$^{131}$I-CE-DTPA") in hamsters bearing GW-39 human tumor xenografts

| | % Injected dose of radioactivity per gram of tissue | | | | |
|---|---|---|---|---|---|
| Tissue | 24 h | 48 h | 72 h | 96 h | 168 h |
| Spleen: | | | | | |
| $^{125}$I-BsAb | 0.25 ± 0.09 | 0.18 ± 0.07 | 0.14 ± 0.12 | 0.09 ± 0.04 | 0.03 ± 0.03 |
| $^{131}$I-CE-DTPA | 0.20 ± 0.05 | 0.13 ± 0.04 | 0.12 ± 0.10 | 0.08 ± 0.03 | 0.03 ± 0.02 |
| Kidney: | | | | | |
| $^{125}$I-BsAb | 0.03 ± 0.08 | 0.26 ± 0.04 | 0.13 ± 0.06 | 0.06 ± 0.02 | 0.02 ± 0.00 |
| $^{31}$I-CE-DTPA | 0.21 ± 0.08 | 0.17 ± 0.03 | 0.10 ± 0.05 | 0.04 ± 0.02 | 0.02 ± 0.01 |
| Lungs: | | | | | |
| $^{125}$I-BsAb | 4.47 ± 6.46 | 0.31 ± 0.08 | 0.22 ± 0.17 | 0.07 ± 0.03 | 0.01 ± 0.00 |
| $^{131}$I-CE-DTPA | 5.20 ± 8.93 | 0.21 ± 0.06 | 0.17 ± 0.15 | 0.05 ± 0.04 | 0.01 ± 0.01 |
| Blood: | | | | | |
| $^{125}$I-BsAb | 0.82 ± 0.36 | 0.84 ± 0.16 | 0.34 ± 0.19 | 0.13 ± 0.06 | 0.02 ± 0.01 |
| $^{131}$I-CE-DTPA | 0.62 ± 0.24 | 0.64 ± 0.11 | 0.30 ± 0.16 | 0.10 ± 0.08 | 0.03 ± 0.02 |

TABLE 3

Biodistributions of 2:1 pre-mixed complex of [$^{125}$I]-hMN-14 Fab' × 734 Fab' [Fab' × Fab'] bispecific antibody ("$^{125}$I-BsAb") and [$^{131}$I]-In-DTPA carboxylesterase ("$^{131}$I-CE-DTPA") in hamsters bearing GW-39 human tumor xenografts

| | % Injected dose of radioactivity per gram of tissue | | |
|---|---|---|---|
| Tissue | 4 h | 24 h | 48 h |
| Tumor: | | | |
| $^{125}$I-BsAb | 0.95 ± 0.53 | 1.38 ± 0.33 | 0.15 ± 0.02 |
| $^{131}$I-CE-DTPA | 0.69 ± 0.36 | 0.68 ± 0.14 | 0.13 ± 0.06 |
| Liver: | | | |
| $^{125}$I-BsAb | 1.15 ± 0.23 | 0.24 ± 0.02 | 0.10 ± 0.00 |
| $^{131}$I-CE-DTPA | 0.75 ± 0.17 | 0.20 ± 0.02 | 0.13 ± 0.01 |
| Spleen: | | | |
| $^{125}$I-BsAb | 1.14 ± 0.05 | 0.25 ± 0.04 | 0.11 ± 0.02 |
| $^{131}$I-CE-DTPA | 0.75 ± 0.03 | 0.15 ± 0.02 | 0.12 ± 0.04 |
| Kidney: | | | |
| $^{125}$I-BsAb | 1.20 ± 0.22 | 0.35 ± 0.06 | 0.11 ± 0.02 |
| $^{131}$I-CE-DTPA | 0.87 ± 0.17 | 0.21 ± 0.04 | 0.08 ± 0.02 |
| Lungs: | | | |
| $^{125}$I-BsAb | 1.38 ± 0.27 | 0.37 ± 0.03 | 0.13 ± 0.02 |
| $^{131}$I-CE-DTPA | 1.00 ± 0.19 | 0.24 ± 0.03 | 0.12 ± 0.02 |
| Blood: | | | |
| $^{125}$I-BsAb | 5.15 ± 0.96 | 1.27 ± 0.33 | 0.29 ± 0.02 |
| $^{131}$I-CE-DTPA | 3.67 ± 0.69 | 0.94 ± 0.21 | 0.34 ± 0.02 |

TABLE 4

Biodistributions of 2:1 pre-mixed complex of [$^{125}$I]-hMN-14 Fab' × 734 Fab' [Fab' × Fab'] bispecific antibody ("$^{125}$I-BsAb") and [$^{131}$I]-In-DTPA-carboxylesterase ("$^{131}$I-CEDTPA") in nude mice bearing GW-39 human tumor xenografts

| | % Injected dose of radioactivity per gram of tissue | | |
|---|---|---|---|
| Tissue | 4 h | 24 h | 48 h |
| Tumor: | | | |
| $^{125}$I-BsAb | 5.87 ± 2.29 | 4.21 ± 0.78 | 2.78 ± 0.56 |
| $^{131}$I-CE-DTPA | 2.53 ± 0.80 | 1.30 ± 0.36 | 1.36 ± 0.41 |
| Liver: | | | |
| $^{125}$I-BsAb | 3.78 ± 0.84 | 0.20 ± 0.03 | 0.07 ± 0.04 |
| $^{131}$I-CE-DTPA | 2.92 ± 0.62 | 0.29 ± 0.05 | 0.14 ± 0.05 |
| Spleen: | | | |
| $^{125}$I-BsAb | 8.82 ± 5.82 | 0.34 ± 0.09 | 0.30 ± 0.44 |
| $^{131}$I-CE-DTPA | 7.17 ± 3.34 | 0.64 ± 0.34 | 0.79 ± 0.68 |
| Kidney: | | | |
| $^{125}$I-BsAb | 8.80 ± 1.09 | 0.40 ± 0.11 | 0.13 ± 0.01 |
| $^{131}$I-CE-DTPA | 3.92 ± 0.77 | 0.26 ± 0.09 | 0.10 ± 0.02 |
| Lungs: | | | |
| $^{125}$I-BsAb | 5.04 ± 1.27 | 0.33 ± 0.09 | 0.09 ± 0.01 |
| $^{131}$I-CE-DTPA | 4.56 ± 1.45 | 0.29 ± 0.07 | 0.10 ± 0.02 |
| Blood: | | | |
| $^{125}$I-BsAb | 11.45 ± 1.94 | 0.38 ± 0.11 | 0.07 ± 0.02 |
| $^{131}$I-CE-DTPA | 12.73 ± 3.55 | 0.52 ± 0.15 | 0.17 ± 0.02 |

TABLE 5

Biodistributions of 2:1 pre-pre-mixed complex of [$^{125}$I]-F6 Fab' (an anti-CEA antibody) × 734 Fab' bispecific antibody ("$^{125}$I-BsAb") [Fab' × Fab'] and [$^{131}$I]-In-DTPA-carboxylesterase ("$^{131}$I-CE-DTPA") in nude mice bearing GW-39 human tumor xenografts

| Tissue | % Injected dose of radioactivity per gram of tissue | | | |
|---|---|---|---|---|
| | 4 h | 24 h | 48 h | 72 h |
| Tumor: | | | | |
| $^{125}$I-BsAb | 4.96 ± 1.19 | 10.01 ± 3.97 | 8.99 ± 2.67 | 11.54 ± 4.06 |
| $^{131}$I-CE-DTPA | 3.28 ± 0.91 | 3.54 ± 1.46 | 3.24 ± 1.02 | 4.50 ± 1.47 |
| Liver: | | | | |
| $^{125}$I-BsAb | 5.15 ± 0.53 | 1.61 ± 0.22 | 0.78 ± 0.12 | 0.41 ± 0.11 |
| $^{131}$I-CE-DTPA | 4.10 ± 0.42 | 1.16 ± 0.16 | 0.70 ± 0.10 | 0.47 ± 0.09 |
| Spleen: | | | | |
| $^{125}$I-BsAb | 10.3 ± 1.65 | 2.43 ± 0.60 | 1.15 ± 0.31 | 0.56 ± 0.12 |
| $^{131}$I-CE-DTPA | 6.68 ± 1.15 | 1.37 ± 0.32 | 0.83 ± 0.20 | 0.53 ± 0.11 |
| Kidney: | | | | |
| $^{125}$I-BsAb | 8.25 ± 0.75 | 2.98 ± 0.31 | 1.06 ± 0.20 | 0.69 ± 0.19 |
| $^{131}$I-CE-DTPA | 5.41 ± 0.32 | 1.64 ± 0.16 | 0.72 ± 0.10 | 0.56 ± 0.14 |
| Lungs: | | | | |
| $^{125}$I-BsAb | 8.57 ± 2.68 | 3.99 ± 1.81 | 1.65 ± 0.24 | 0.83 ± 0.18 |
| $^{131}$I-CE-DTPA | 6.85 ± 0.44 | 2.21 ± 1.04 | 1.21 ± 0.17 | 0.78 ± 0.20 |
| Blood: | | | | |
| $^{125}$I-BsAb | 28.54 ± 1.81 | 11.82 ± 1.25 | 5.24 ± 0.78 | 2.48 ± 0.76 |
| $^{131}$I-CE-DTPA | 21.35 ± 1.23 | 7.59 ± 0.76 | 3.88 ± 0.51 | 2.26 ± 0.49 |

TABLE 6

Biodistributions of 2:1 pre-mixed complex of [$^{125}$I]-F6 Fab' (an anti-CEA antibody) × 734 Fab' bispecific antibody ("$^{125}$I-BsAb") [Fab' × Fab'] and [$^{131}$I]-In-IMP222-carboxylesterase ("$^{131}$I-CE-IMP222") in nude mice bearing GW-39 human tumor xenografts

| Tissue | % Injected dose of radioactivity per gram of tissue | | | |
|---|---|---|---|---|
| | 4 h | 25 h | 48 h | 120 h |
| Tumor: | | | | |
| $^{125}$I-BsAb | 5.17 ± 2.10 | 11.51 ± 1.73 | 11.08 ± 4.37 | 3.66 ± 1.26 |
| $^{131}$I-CE-DTPA | 2.83 ± 1.06 | 3.96 ± 0.71 | 4.41 ± 1.71 | 2.42 ± 0.75 |
| Liver: | | | | |
| $^{125}$I-BsAb | 4.84 ± 0.85 | 1.59 ± 0.12 | 0.62 ± 0.08 | 0.16 ± 0.03 |
| $^{131}$I-CE-DTPA | 3.72 ± 0.63 | 1.14 ± 0.05 | 0.50 ± 0.07 | 0.19 ± 0.03 |
| Spleen: | | | | |
| $^{125}$I-BsAb | 10.89 ± 3.25 | 2.46 ± 0.92 | 0.89 ± 0.09 | 0.20 ± 0.05 |
| $^{131}$I-CE-DTPA | 6.98 ± 2.28 | 1.44 ± 0.43 | 0.61 ± 0.08 | 0.22 ± 0.06 |
| Kidney: | | | | |
| $^{125}$I-BsAb | 7.53 ± 1.90 | 2.38 ± 0.39 | 1.01 ± 0.16 | 0.12 ± 0.02 |
| $^{131}$I-CE-DTPA | 4.71 ± 1.09 | 1.36 ± 0.23 | 0.68 ± 0.12 | 0.17 ± 0.03 |
| Lungs: | | | | |
| $^{125}$I-BsAb | 8.55 ± 1.55 | 2.75 ± 0.67 | 0.99 ± 0.16 | 0.07 ± 0.02 |
| $^{131}$I-CE-DTPA | 6.31 ± 1.18 | 1.80 ± 0.47 | 0.78 ± 0.15 | 0.20 ± 0.03 |
| Blood: | | | | |
| $^{125}$I-BsAb | 24.41 ± 2.46 | 8.24 ± 0.71 | 2.80 ± 0.26 | 0.17 ± 0.07 |
| $^{131}$I-CE-DTPA | 21.38 ± 2.87 | 6.93 ± 0.66 | 3.11 ± 0.28 | 0.77 ± 0.19 |

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference in their entirety.

REFERENCES THAT MAY BE OF INTEREST

European Patent No. 0595743.

Auzenne, E., Donato, N. J., Li, C., Leroux, E., Price, R. E., Farquhar, D. and Klostergaard, J. Superior therapeutic profile of poly-L-glutamic acid-paclitaxel copolymer compared with taxol in xenogeneic compartmental models of human ovarian carcinoma. *Clin. Cancer Res.*, 8:573-581, 2002.

Bagshawe, K. D. Antibody-directed enzyme prodrug therapy for cancer: its theoretical basis and application. *Mol. Med. Today*, 1:424-431, 1995.

Bagshawe, K. D., Sharma, S. K., Springer, C. J., Antoniw, P., Boden, J. A., Rogers, G. T., Burke, P. J., Melton, R. G. and Sherwood, R. F. Antibody directed enzyme prodrug therapy (ADEPT): clinical report. *Dis. Markers*, 9:233-238, 1991.

Barbet et al., Pretargeting with the affinity enhancement system for radioimmunotherapy. *Cancer Biother. Radiopharm.*, 14:153-166, 1999.

Biela, B. H., Khawli, L. A., Hu, P. and Epstein, A. L. Chimeric TNT-3/human betaglucuronidase fusion proteins for antibody-directed enzyme prodrug therapy (ADEPT). *Cancer Biother, Radiopharm.*, 18:339-353, 2003.

Bonardi et al., Delivery of saporin to human B-cell lymphoma using bispecific antibody: Targeting via CD22 but not CD19, CD37, or immunoglobulin results in efficient killing. *Cancer Res.*, 53:3015-3021, 1993.

Casey et al., Preparation, characterisation and tumour targeting of cross-linked divalent and trivalent anti-tumour Fab' fragments. *Br. J. Cancer.*, 74:1397-1405, 1996.

Chen, B. M., Cheng, T. L., Tzou, S. C. and Roffler, S. R., "Potentiation of antitumor immunity by antibody-directed enzyme prodrug therapy," *Int. J. Cancer*, 94:850-858, 2001.

Darks, M. K., Morton, C. L., Krull, E. J., Cheshire, P. J., Richmond, L. B., Naeve, C. W., Pawlik, C. A., Houghton, P. J. and Potter, P. M. Comparison of activation of CPT-11 by rabbit and human carboxylesterases for use in enzyme/prodrug therapy. *Clin. Cancer Res.*, 5:917-924, 1999.

Deckert, P. M., Renner, C., Cohen, L. S., Jungbluth, A., Ritter, G., Bertino, J. R., Old, L. J. and Welt, S. A33scFv-cytosine deaminase: a recombinant protein construct for antibody-directed enzyme-prodrug therapy. *Br. J. Cancer*, 88:937-939, 2003.

de Bont, D. B., Leenders, R. G., Haisma, H. J., van der Meulen-Muileman, I. and Scheeren, H. W. Synthesis and biological activity of beta-glucuronyl carbamate-based prodrugs of paclitaxel as potential candidates for ADEPT. *Bioorg. Med. Chem.*, 5:405-414, 1997.

de Graaf, M., Boven, E., Scheeren, H. W., Haisma, H. J. and Pinedo, H. M. Betaglucuronidase-mediated drug release. *Curr. Pharm. Des.*, 8:1391-1403, 2002.

Denny, W. A. Prodrug strategies in cancer therapy. *Eur. J. Med. Chem.*, 36:577-595, 2001.

Francis, R. J., Sharma, S. K., Springer, C., Green, A. J., Hope-Stone, L. D., Sena, L., Martin, J., Adamson, K. L., Robbins, A., Gumbrell, L., O'Malley, D., Tsiompanou, E., Shahbakhti, H., Webley, S., Hochhauser, D., Hilson, A. J., Blakey, D., Begent, R. H. A phase I trial of antibody directed enzyme prodrug therapy (ADEPT) in patients with advanced colorectal carcinoma or other CEA producing tumours. *Br. J. Cancer*, 87:600-607, 2002.

French. Production of bispecific and trispecific F(ab)$_2$ and F(ab)$_3$ antibody derivatives. *Methods Mol. Biol.*, 80:121-134, 1998.

Gestin et al., Two-step targeting of xenografted colon carcinoma using a bispecific antibody and 188Re-labeled bivalent hapten: biodistribution and dosimetry studies. *J. Nucl. Med.*, 42:146-153, 2001.

Hillairet de Boisferon et al., Enhanced targeting specificity to tumor cells by simultaneous recognition of two antigens. *Bioconjug Chem.*, 11:452-460, 2000.

Houba, P. H., Boven, E., van der Meulen-Muileman, I. H., Leenders, R. G., Scheeren, J. W., Pinedo, H. M. and Haisma, H. J. Pronounced antitumor efficacy of doxorubicin when given as the prodrug DOX-GA3 in combination with a monoclonal antibody beta-glucuronidase conjugate. *Int. J. Cancer*, 91:550-554, 2001.

Jung M. Antibody directed enzyme prodrug therapy (ADEPT) and related approaches for anticancer therapy. *Mini Rev. Med. Chem.*, 1:399-407, 2001.

Kan et al., Thioether-bonded constructs of Fab'gamma and Fc gamma modules utilizing differential reduction of interchain disulfide bonds. *J Immunol.*, 166:1320-1326, 2001.

LeDoussal et al., Enhanced in vivo targeting of an asymmetric bivalent hapten to double-antigen positive mouse B cells with monoclonal antibody conjugate cocktails. *J. Immunol.*, 146:169-175, 1991.

Li, C., Yu, D. F., Newman, R. A., Cabral, F., Stephens, L. C., Hunter, N., et al. Complete regression of well-established tumors using a novel water-soluble poly(L-glutamic acid)-paclitaxel conjugate. *Cancer Res.*, 58:2404-2409, 1998.

Melton, R. G., Boyle, J. M., Rogers, G. T., Burke, P., Bagshawe, K. D. and Sherwood, R. F. Optimisation of small-scale coupling of A5B7 monoclonal antibody to carboxypeptidase G2. *J. Immunol Methods*, 158:49-56, 1993.

Schott et al., Preparation, characterization, and in vivo biodistribution properties of synthetically cross-linked multivalent antitumor antibody fragments. *Bioconjug. Chem.*, 4:153-165, 1993.

Schoonjans et al., Fab chains as an efficient heterodimerization scaffold for the production of recombinant bispecific and trispecific antibody derivatives. *J. Immunol.*, 165:7050-7057, 2000.

Schoonjans et al., A new model for intermediate molecular weight recombinant bispecific and trispecific antibodies by efficient heterodimerization of single chain variable domains through fusion to a Fab-chain. *Biomol. Eng.*, 17:193-202, 2001.

Sharma, S. K., Bagshawe, K. D., Springer, C. J., Burke, P. J., Rogers, G. T., Boden, J. A., Antoniw, P., Melton, R. G. and Sherwood R F. Antibody directed enzyme prodrug therapy (ADEPT): a three phase system. *Dis. Markers*, 9:225-231, 1991.

Sharma, S. K., Bagshawe, K. D., Burke, P. J., Boden, R. W. and Rogers, G. T. Inactivation and clearance of an anti-CEA carboxypeptidase G2 conjugate in blood after localisation in a xenograft model. *Br. J. Cancer*, 61:659-662, 1990.

Spooner, R. A., Friedlos. F., Maycroft, K., Stribbling, S. M., Roussel, J., Brueggen, J., Stolz, B., O'Reilly, T., Wood, J., Matter, A., Marais, R. and Springer, C. J. A novel vascular endothelial growth factor-directed therapy that selectively activates cytotoxic prodrugs. *Br. J. Cancer*, 88:1622-1630, 2003.

Springer, C. J., Antoniw, P., Bagshawe, K. D. and Wilman, D. E. Comparison of half-lives and cytotoxicity of N-chloroethyl-4-amino and N-mesyloxyethyl-benzoyl compounds, products of prodrugs in antibody-directed enzyme prodrug therapy (ADEPT). *Anticancer Drug Des.*, 6:467-479, 1991.

Springer, C. J. and Niculescu-Duvaz, I. Antibody-directed enzyme prodrug therapy (ADEPT): a review. *Adv. Drug Deliv. Rev.*, 26:151-172, 1997.

Tietze, L. F., Herzig, T., Fecher, A., Haunert, F. and Schuberth, I. Highly selective glycosylated prodrugs of cytostatic CC-1065 analogues for antibody-directed enzyme tumor therapy. *Chembiochem.* 2:758-765, 2001.

Tietze, L. F., Lieb, M., Herzig, T., Haunert, F. and Schuberth, I. A strategy for tumor-selective chemotherapy by enzymatic liberation of seco-duocarmycin SA-derivatives from nontoxic prodrugs. *Bioorg. Med. Chem.*, 9:1929-1939, 2001.

Werlen et al., Preparation of a trivalent antigen-binding construct using polyoxime chemistry: improved biodistribution and potential for therapeutic application. *Cancer Res.*, 56:809-815, 1996.

Wolfe, L. A., Mullin, R. J., Laethem, R., Blumenkopf, T. A., Cory, M., Miller, J. F., Keith, B. R., Humphreys, J. and Smith, G. K. Antibody-directed enzyme prodrug therapy with the T268G mutant of human carboxypeptidase A1: in vitro and in vivo studies with prodmgs of methotrexate and the thymidylate synthase inhibitors GW 1031 and GW1843. *Bioconjug. Chem.*, 10:38-48, 1999.

Xu, G. and McLeod, H. L. Strategies for enzyme/prodrug cancer therapy. *Clin. Cancer Res.*, 7:3314-3324, 2001.

What is claimed is:

1. A method for treating target cells, tissues or pathogens in a subject comprising:
 a) mixing
  (i) a multispecific targeting protein comprising at least one target-binding site and one hapten-binding site, and
  (ii) a hapten-enzyme covalent conjugate comprising two haptens linked by a peptide of from 2 to 10 amino acid residues in length, wherein the hapten-enzyme covalent conjugate is a carboxylesterase-IMP222 (Ac-Cys-Lys(DTPA)-Tyr-Lys(DTPA)-NH2 (SEQ ID NO: 2));
 b) forming a non-covalently bound complex between the multispecific targeting protein and the hapten-enzyme covalent conjugate, wherein the non-covalently bound complex is formed prior to administration of the complex to a subject;
 c) administering the non-covalently bound complex to a subject; and
 d) administering to the subject a chemotherapeutic drug or prodrug, capable of being converted to a more active drug by the enzyme attached to the non-covalently bound complex.

2. The method of claim 1, wherein said multispecific targeting protein is a multispecific antibody or a multispecific antibody fragment.

3. The method of claim 1, wherein said non-covalent complex is formed immediately before it is administered to the subject.

4. The method of claim 2, wherein said multispecific targeting protein is an anti-CEA×anti-indium-DTPA F(ab')$_2$ ×Fab'.

5. The method of claim 1, wherein said non-covalent complex is stored after it is formed and before it is administered to the subject.

6. The method of claim 1, wherein said non-covalent complex is injected intravenously, intravesically, intra-arterially, intra-tumorally or intraperitoneally into said subject.

7. The method of claim 1, wherein said non-covalent complex binds to a cellular tumor-associated antigen.

8. The method of claim 7, wherein the cellular tumor-associated antigen is selected from the group consisting of AFP (alpha fetoprotein), carbonic anhydrase IX, BrE3-antigen, CD1, CD1a, CD3, CD5, CD15, CD16, CD19, CD20, CD21, CD22, CD23, CD25, CD30, CD37, CD45, CD74, CD79a, CD80, HLA-DR, NCA95, NCA90, HCG and its subunits, CEA (CEACAM-5), CEACAM-6, CSAp, EGFR, EGP-1, EGP-2, Ep-CAM, folate receptor, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, MUC16, PAM-4-antigen, PSA, PSMA, RS5, S100, TAG-72, p53, tenascin, insulin growth factor-1 (IGF-1), T101, Tn antigen, Thomson-Friedenreich antigens, tumor necrosis antigens, VEGF, placenta growth factor (P1 GF), 17-1A-antigen, ED-B fibronectin, bc1-2, and an oncogene product.

9. The method of claim 1, wherein the hapten-enzyme covalent conjugate comprises two haptens linked by a peptide of from 2-5 amino acid residues in length.

10. The method of claim 1, wherein the hapten-enzyme covalent conjugate comprises two haptens linked by a peptide of 3 amino acid residues in length.

11. The method of claim 1, wherein the carboxylesterase is rat, mouse, rabbit, porcine or human carboxylesterase.

12. The method of claim 1, further comprising administering a clearing agent to the subject after administration of the non-covalent complex and before administration of the chemotherapeutic drug or prodrug.

13. The method of claim 1, wherein the multispecific targeting protein is murine, chimeric, humanized, human, or a mixture of thereof.

14. The method of claim 12, wherein the clearing agent is an antibody directed against an epitope of the multispecific targeting protein/hapten-enzyme complex.

15. The method of claim 12, wherein the clearing agent is an anti-idiotypic antibody to the multispecific targeting protein.

16. The method of claim 15, wherein the clearing agent is a carbohydrate-derivatized anti-idiotypic antibody to the multispecific targeting protein.

17. The method of claim 15, wherein the clearing agent is a galactosylated anti-idiotypic antibody to the multispecific targeting protein.

18. The method of claim 1, wherein the chemotherapeutic prodrug has greater aqueous solubility than the active drug produced by the enzyme.

19. The method of claim 1, wherein the chemotherapeutic prodrug is a prodrug of a camptothecin, doxorubicin, paclitaxel, actinomycin, maytansine, calicheamicin or epothiline class of drug.

20. The method of claim 19, wherein the chemotherapeutic prodrug is a prodrug of SN-38.

21. The method of claim 20, wherein the chemotherapeutic prodrug is CPT-11.

22. The method of claim 1, wherein said subject is a human.

23. The method of claim 1, wherein the multispecific targeting proteina bispecific antibody or bispecific antibody fragment, comprising at least one target-binding site and one hapten-binding site.

* * * * *